United States Patent [19]

Wittwer et al.

[11] Patent Number: 4,609,403
[45] Date of Patent: Sep. 2, 1986

[54] FOAM SOFT GELATIN CAPSULES AND THEIR METHOD OF MANUFACTURE

[75] Inventors: Fritz Wittwer, Lupsingen, Switzerland; Jean-Philippe Mayer, Colmar, France

[73] Assignee: Warner-Lambert Company, Morris Plains, N.J.

[21] Appl. No.: 588,408

[22] Filed: Mar. 12, 1984

[51] Int. Cl.⁴ .......................... A61J 3/07; A61K 9/48; C08J 9/30; C08L 89/04
[52] U.S. Cl. .................... 106/122; 106/136; 264/50; 424/14; 424/37; 424/DIG. 14; 424/DIG. 15; 425/804
[58] Field of Search ............. 264/50; 106/136, 122; 425/804; 222/107; 424/14, 37, DIG. 14, DIG. 15

[56] References Cited

U.S. PATENT DOCUMENTS

| | | | |
|---|---|---|---|
| 650,760 | 5/1900 | Metcalf | 424/37 |
| 1,122,089 | 12/1914 | Estes | 424/37 X |
| 1,701,811 | 2/1929 | Keller | 424/37 X |
| 2,390,088 | 12/1945 | Fox et al. | 424/37 X |
| 2,973,301 | 2/1961 | Klotz | 424/37 |
| 2,990,334 | 6/1961 | Graham | 424/37 |
| 3,126,321 | 3/1964 | Kurtz | 424/37 |
| 3,555,132 | 1/1971 | Benning | 264/50 |
| 3,765,917 | 10/1973 | Hijiya et al. | 106/136 X |
| 3,823,816 | 7/1974 | Controulis et al. | 424/37 X |
| 3,851,051 | 11/1974 | Miskel et al. | 424/37 |
| 4,045,239 | 8/1977 | Hammer et al. | 106/136 X |
| 4,086,331 | 4/1978 | Neumann | 424/45 |
| 4,325,761 | 4/1982 | Pace | 156/69 |
| 4,331,547 | 5/1982 | Stotts et al. | 106/130 X |
| 4,333,957 | 6/1982 | Okajima et al. | 424/14 X |
| 4,403,461 | 9/1983 | Goutard et al. | 53/282 |
| 4,428,927 | 1/1984 | Ebert et al. | 424/37 |
| 4,500,358 | 2/1985 | Mayer et al. | 106/122 |
| 4,532,126 | 7/1985 | Ebert et al. | 424/37 X |

FOREIGN PATENT DOCUMENTS 3107627  1/1982  Fed. Rep. of Germany .

OTHER PUBLICATIONS

Jones, R. T. "Pharmaceutical Gelatin-Applications" in *Process Biochemistry*, Jul. 1971, pp. 19-22.

Primary Examiner—Philip Anderson
Attorney, Agent, or Firm—Alan H. Spencer; Stephen Raines

[57] ABSTRACT

Single piece capsules, produced, filled and sealed in a single operation, also known as soft shell capsules, having a special foam wall structure, obtained by a microdispersion of a gas in an aqueous mixture of dry gelatin and one or more plasticizers.

The capsules are formed by processing, on soft shell capsule manufacturing machines, foamed ribbons, cast from a film forming mixture obtained by a microdispersion of a gas in an aqueous mixture of gelatin and one or more plasticizers; optionally with the inclusion of a coloring agent, an opacifying agent, a foam stabilizer, a gelatin extender, a preservative, a flavoring agent, a sweetening agent, or a drug.

By a suitable choice of the gas proportion in the capsule wall and its microdispersion level, it is possible, within certain limits, to control the capsule wall disintegration speed and its opacity. Also, the inclusion of gas bubbles in the capsule wall decreases the gelatin material required for foam soft gelatin capsules and provides energy saving during production due to a faster drying of the capsule wall, thereby achieving lower costs for the production of said foam soft gelatin capsules over conventional soft gelatin capsules.

33 Claims, 2 Drawing Figures

FOAM SOFT GELATIN CAPSULES AND THEIR METHOD OF MANUFACTURE

SUMMARY OF THE INVENTION

The present invention discloses methods to produce foam soft gelatin capsules. More particularly, the invention relates to pharmaceutically acceptable single piece capsules; for the dosage of liquid, waxy, pasty or solid drug formulations; which are produced, filled and sealed successively in a single operation. The capsules are produced by processing, on soft capsule manufacturing machines, foamed ribbons cast from a gelatin foam, said gelatin foam being obtained by a homogeneous microdispersion of gas in an aqueous mixture of gelatin and one or more plasticizers.

In this application, when the term "gelatin" is used, it is also understood to include other proteins similar to gelatin in physical and chemical properties combined with starch or derivatives thereof.

As used herein, the term "foam soft gelatin capsules" means such capsules, obtained on soft capsules manufacturing machines from gelatin foams, the wall of which being formed by a homogeneous microdispersion of gas in a mixture of dry gelatin and one or more plasticizers.

It is known (reference: article entitled Pharmaceutical Gelatin - Applications by R. T. Jones, *Process Biochemistry*, pages 19–22, July 1971), that conventional soft gelatin capsules are a preferred form of administration for medicaments and similar products; especially liquids, pastes, solids dispersed in liquids; or dry solids. Soft gelatin capsules also possess particular advantages for substances which require total protection from air and light, because the gelatin is completely sealed around the contents. An important example is for the encapsulation of vitamins, which has resulted in a high degree of stability thereof.

The disintegration speed of soft gelatin capsules can vary considerably depending upon the composition of the contents. For example, the disintegration of soft gelatin capsules containing a lipophilic medicament is delayed because of the lipophilic properties of the contents. The rapid release of the medicament is thereby impaired which can have a detrimental effect on its bio-availability.

Processes have been disclosed for the filling with liquids or pastes, with a subsequent sealing of two-piece hard shell gelatin capsules. (U.S. Pat. No. 4,325,761 and German Patent No. DE 31,07,627). Such two-piece hard shell gelatin capsules are characterized by an about three times thinner wall than soft gelatin capsules, resulting, for the dosage of an equivalent drug amount, in a lower manufacturing cost (less raw material consumption) and in a faster disintegration.

An objective of this invention is to modify the capsule wall of soft gelatin capsules provided for medicinal and other purposes in such a manner that a control, particularly an acceleration, of the capsule disintegration can be achieved in a simple manner.

Another objective of this invention is to modify the capsule wall of said soft gelatin capsules so as to save significant quantities of raw material for an equivalent capsule dimension, shape and wall thickness.

Many additives used in pharmaceutical materials are now being critically examined. For example, titanium dioxide, commonly used as an opacifier in soft gelatin capsules, is under examination as to whether it is pharmaceutically acceptable. It is therefore a further objective of this invention to modify the capsule wall of said soft gelatin capsules in such a manner that it would be opaque without addition of titanium dioxide or other similar chemicals. Such a soft gelatin capsule could therefore contain only natural and biodegradable products. This would be an important advantage over conventional soft gelatin capsules.

As disclosed in applicants' copending application U.S. Ser. No. 438,147) filed Oct. 29, 1982, and now abandoned the disclosure of which is incorporated herein by reference, these objectives could be achieved in the field of two-piece hard shell gelatin capsules, having telescopically joined body and cap portions, by forming the wall of said capsules by dip-molding into a gelatin foam obtained by microdispersion of a suitable gas in gelatin. As a consequence of those discoveries, it was also possible to achieve the objectives of the present invention and to provide foam soft gelatin capsules: which contain substantially less raw material, which are opaque without additives such as titanium dioxide, and which disintegrate at a particularly higher speed that can be controlled. Said foam soft gelatin capsules are characterized in that the material forming the capsule wall is a gelatin foam obtained by microdispersion of a suitable gas in a mixture of gelatin and one or more plasticizers, optionally with the inclusion of additives leading to optimal or specific qualities.

DESCRIPTION OF THE PRIOR ART

Prior art for gelatin based foams is contained in the following patents:

1. U.S. Pat. No. 3,555,132, issued Jan. 12, 1971 to C. J. Benning, which discloses a process for producing an aldehyde-hardened gelatin foam consisting of the steps of:

(a) adding 4 to 24 parts of said aldehyde to a solution of 50% by weight of gelatin in water to insolubilize the gelatin;

(b) beating the wetted solution into a foam;

(c) shaping the foam by placing it in a mold;

(d) removing the shaped foam from the mold; and (e) simultaneously heating and drying the foam at temperatures between about 51° to 93° C.

The resulting stiff and rigid foam blocks have densities of 0.065 to 0.080 g/cm$^3$ and are intended for shockabsorbing and insulating purposes.

2. U.S. Pat. No. 4,086,331, issued Apr. 25, 1978 to P. Neumann, which discloses a composition and a method for the generation of gelatin-based stabilized foams for use in medicine for the treating of burns and in agriculture for the coating of plants.

Said compositions comprise an aqueous solution of 0.1% to 3% by weight of gelatin; 0.01 to 0.2% by weight of an anionic surface active agent; an amount sufficient to stabilize said gelatin based foam up to 1% by weight of a water soluble ferrous salt; and an amount of glutaraldehyde sufficient to maintain said composition in liquid state.

Said foaming method consists of passing a stream of air or a gas through orifices or sintered metal or of aerosol generation at temperatures of between about 5° to 30° C. The resulting foams have densities in the wet state between 0.0035 to 0.20 g/cm$^3$ and bubble diameters are in a broad range of between about 1 mm to 10 mm.

3. U.S. Pat. No. 4,331,547, issued May 25, 1982 to E. J. Stotts and G. S. Arbuthnot discloses a thermal insulating foam made from a collagen protein such as animal glue; and a method of production thereof.

The dry density of the foam is of the order of 0.004 to 0.008 g/cm$^3$.

DETAILED DESCRIPTION OF THE INVENTION

The gelatin foams, suitable to obtain foam soft gelatin capsules according to the present invention, are made from a viscous plasticized gelatin mass, basically composed of gelatin, with one or more plasticizers and water.

The ratio by weight of dry plasticizer to dry gelatin is in a range of about between 0.3 to 1.8, preferably in a range of about between 0.4 to 0.75.

The ratio by weight of water to dry gelatin is in a range of about between 0.8 to 1.6, preferably in a range of about between 1 and 1.3.

Different grades of pure gelatins or mixtures thereof can be used at pH values about between 4.0 to 10.0, and preferably between 4.0 to 7.0.

The plasticizers may be selected from the following groups:

a. Poly-hydroxy-alcohols including glycerol, sorbitol, and mannitol;

b. Dialkylphtalates preferably where alkyl is butyl;

c. Lower alkyl citrates wherein lower alkyl has 1 to 6 carbon atoms;

d. Glycols and polyglycols including polyethyleneglycol with a molecular weight range of about 200 to 40,000 dalton, methoxy-propylene-glycol, and 1,2-propyleneglycol;

e. Esters of polyhydroxy-alcohols including mono-, di- and tri-acetate of glycerol;

f. Ricinoleic acid and esters thereof; and g. Related materials and mixtures of the above.

In the manufacture of conventional soft gelatin capsules and of foam soft gelatin capsules, the solid constituents of the gelatin mass are preferably mixed with the chilled liquid constituents; the resulting fluffy mass is melted under reduced pressure at about 65° to 95° C., and then the melt maintained at about 50° to 80° C. Other appropriate mixing and melting procedures may also be used for the purpose of the present invention.

Since the additional foaming step considerably increases the viscosity of the gelatin mass, and, due to the higher ratio water to gelatin, the viscosity of the melt is lower in the present invention than for the melt used in the manufacture of conventional soft gelatin capsules.

Gelatin foams according to the present invention may be produced according to any of a number of methods, wherein air or a gas; such as nitrogen, oxygen, argon, carbon dioxide or another suitable gas or a mixture thereof; is microdispersed within the gelatin melt. This microdispersion is generally obtained by direct application of mechanical energy, in an operation where the gelatin melt is brought and kept in violent motion in the presence of the gas. This may be done batchwise or continuously, in open or closed reservoirs.

BRIEF DESCRIPTION OF THE DRAWINGS

The invention both as to its organization and method of operation, together with further objects and advantages thereof, will best be understood by reference to the following specification and in conjunction with the accompanying drawings, in which.

DETAILED DESCRIPTION OF THE INVENTION

Figure 1:
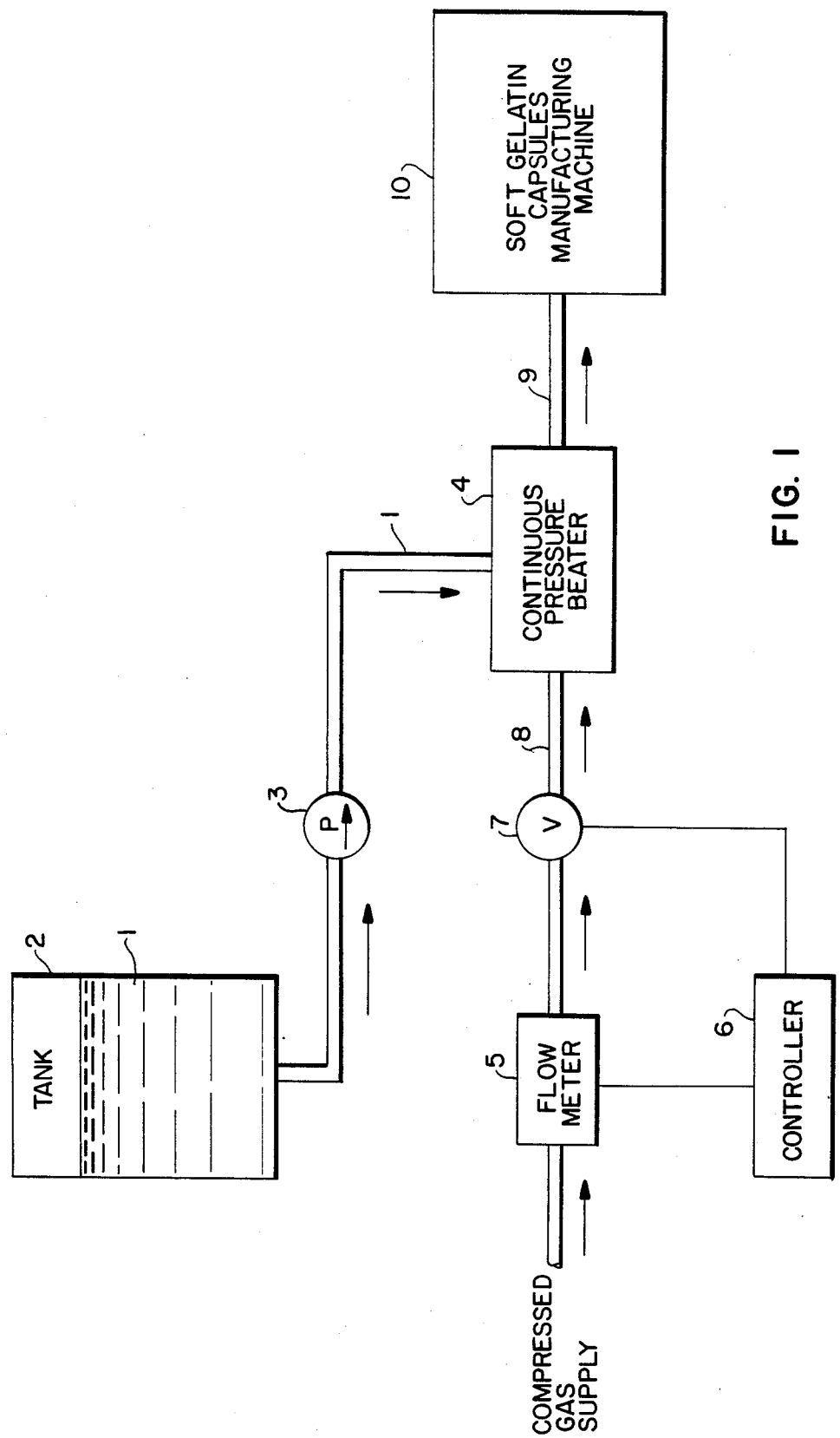
FIG. 1 is a flow chart of one embodiment of the process of this invention.

FIG. 1 illustrates an embodiment of the present invention, whereby the gelatin melt 1, maintained in a water-jacketted tank 2 at a temperature range of between 50° to 80° C., is metered under pressure by a pump 3 into the mixing head of a continuous pressure beater or whipper 4, together with the required amount of gas 8, metered by a flow controlling system composed of a flow meter 5 connected with a flow controller 6 which controls a valve 7 to maintain a constant gas flow rate if upstream or downstream conditions change. The gas to gelatin ratio in the foam is controlled by corresponding injection rates. The microdispersion of the gas bubbles in the gelatin is accomplished during the axial transit of the gelatin/gas mixture through the mixing head of the continuous pressure beater 4 by the shearing effect produced within this mixing head by the rotation of a rotor in a stator, both being fitted with a high number of teeth or holes. The microdispersion level of the gas bubbles and the homogeneity of the gelatin foam is controlled by the rotation speed of the rotor, the number of teeth or holes, the configuration of the mixing head and the contact time of the gelatin-melt and gas mixture within the mixing head. Since this operation generates considerable heat, and since the gelatin foam must be kept below a controlled temperature to avoid gelatin degradation, the mixing head of the continuous pressure beater 4 is preferably equipped with a heat exchanger.

When working under constant controlled conditions, the foaming system shown in FIG. 1 delivers a uniform gelatin foam directly to a soft gelatin capsules manufacturing machine, wherein said foam is further processed to make foam soft gelatin capsules.

Soft gelatin capsules manufacturing machines may be adapted to the manufacture of foam soft gelatin capsules from gelatin foams. For example, the following may be adapted: reciprocating die apparatus developed by the Norton Company, Worcester, Mass.; or the Accogel apparatus developed by the Lederle Laboratories Division of the American Cyanamid Company, Pearl River, N.Y., modified for an accurate filling with powdered dry solids; or the rotary die apparatus of R. P. Scherer Corporation, Detroit, Mich., and described in following reference:

L. Lachman, H. A. Lieberman, J. L. Kanig, "The Theory and Practice of Industrial Pharmacy," 2nd ed., pages 404 to p. 420, published by Lea and Febiger, Philadelphia, Pa., 1976.

Referring again to FIG. 1. In the present invention, instead of a plasticized melt of gelatin, it is the gelatin foam 9 produced by the continuous pressure beater 4 which is fed by gravity to one or both spreader boxes of a manufacturing machine, which controls the flow of the gelatin foam onto air-cooled rotating drums. Foamed and plasticized gelatin ribbons of controlled thickness are formed and fed, for example, through the rotary die process, where the foam soft gelatin capsules are formed, filled and sealed on soft capsules machines. Immediately after manufacture, 35 the foam soft gelatin capsules are subjected, like conventional soft gelatin capsules, to appropriate washing and drying steps.

Figure 2:
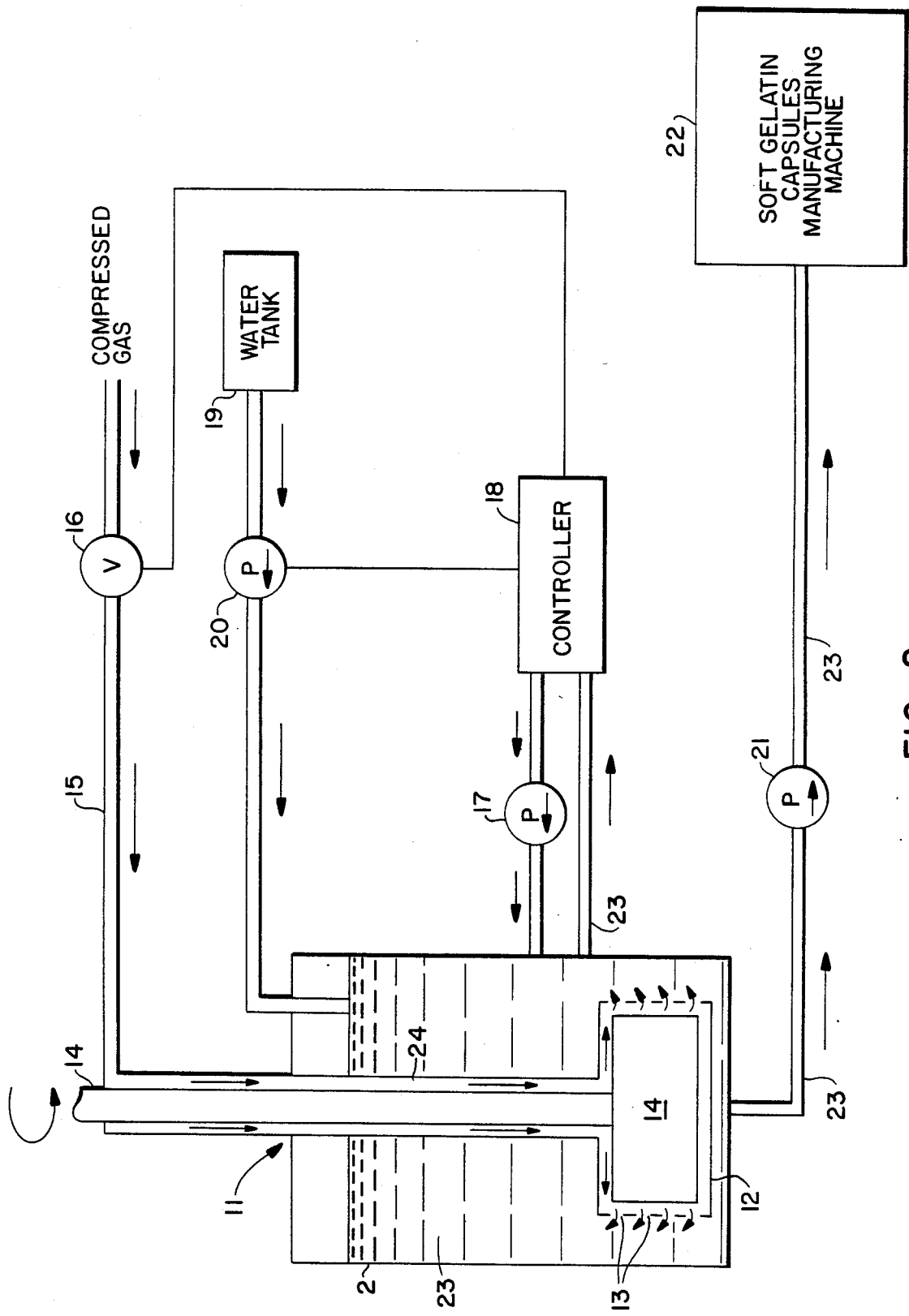
FIG. 2 is a flow chart of a second embodiment depicts a batch process of the variation of the subject invention.

FIG. 2 discloses another embodiment wherein the gelatin foam 23 is directly generated, batchwise, in the open tank 2, fitted with a heat exchanging water jacket, and which initially contains a batch of gelatin melt.

Foaming is accomplished by means of a centrifugal emulsifier 11, comprising a stator 12 perforated with small holes 13, and a rotor 14.

During a first step, a gas flow 15, controlled by a valve 16, is introduced through the hollow axis 24 into the stator 12, where the gas is mixed with gelatin and micronized by the rotor 14, rotating at high speed and forcing the gas/gelatin mixture through the holes 13 of the perforated stator 12.

The resulting gelatin foam 23 is circulated by means of a pump 17 through a controller 18, where viscosity, density and temperature of the foam are simultaneously measured in-line. A given foam quality is completely characterized by a set of values of these three parameters. According to the measured parameters, a calculating device included in controller 18 controls gas addition into the gelatin foam through the valve 16 and/or water addition by by means of the pump 20 until the required gelatin foam quality is obtained.

In a second step, a metering pump 21 feeds gelatin foam 23 into a soft gelatin capsules manufacturing machine, where foam soft gelatin capsules are produced.

As described above, the foam quality of the batch is continuously measured by means of the controller 18 and accordingly regulated for gas and water addition by means of the valve 16 and the pump 20, respectively. The microdispersion level of the gas bubbles in the gelatin foam and the homogeneity of said gelatin foam are to a considerable extent controlled by the rotation speed of the rotor, the dimensions of the perforations of the stator and the distance the between rotor and the stator.

After usage of the gelatin foam batch, the pump 21 is stopped and a new tank 2 containing another foam batch is hooked in line, replacing the empty one, without interruption of the foam soft gelatin capsules manufacturing.

Other foaming equipment may be successfully adapted for the generation of gelatin foams, such as whipping or beating equipment, especially those commonly used in the food industry, provided that the characteristics of such equipment may be adapted to obtain a sufficient microdispersion level of the gas bubbles to avoid any hole in the capsule wall and to ensure an acceptable opacity of said wall.

Suitable gelatin foams for making foam soft gelatin capsules according to the present invention are characterized by a gas content of between about 10 to 66% vol/vol. of the gelatin foam, preferably 23 to 56%; a viscosity of between about 1,000 and 30,000 centipoises when measured at 60° C., preferably 5,000 to 15,000 centipoises when measured at 60° C. For obtaining a desired opacity, the diameter of the dispersed gas bubbles is between about 0.1 to 200 microns, preferably 1 to 50 microns. The temperature, upon reaching the soft gelatin capsules manufacturing machine inlet, is between 40° to 95° C., and preferably between 55° to 70° C.

In some case, particularly when more diluted gelatin solutions are used, foam stabilizing agents may be added at varying concentrations. Amounts of about 0.01 to 5% based upon the weight of gelatin have been found effective. Suitable foam stabilizing agents include:

viscosity increasing agents selected from a group consisting of alginic acid and salts thereof; xanthan; cellulose derivatives including carboxymethylcellulose, hydroxypropycellulose, hydroxypropylmethylcellulose, and microcrystalline cellulose;

vegetable gums consisting of carrageenates, pectin, and agar;

proteins consisting of egg white and its derivatives, including pan-dried or spraydried egg albumin, and hydrolyzed animal proteins;

esters consisting of sucrose esters, fatty acid esters and ethoxylates thereof, including polyglycerol and sorbitol derivatives thereof; glycerides and derivatives thereof including succinyl monoglycerides; acetic-, lactic-, citric-, or acetylated tartaric acid esters of monoglycerides, glycosides, lanolin and its derivatives, and mixtures thereof;

non-ionic surfactants consisting of fatty acid alkylolamides or ethoxylates thereof; amines and amine oxides with at least one long chain substituent of between 8 to 18 carbon atoms, and particularly N,N-dimethyldodecylamine; linear or branched long chain alcohols with between 8 to 18 carbon atoms and particularly lauryl alcohol; and mixtures thereof;

anionic surfactants selected from alkylarylsulphonates, the alphatic chain, linear or branched, bearing 8 to 14 carbon atoms, the aromatic nucleus being benzene or toluene, the cation being sodium, ammonium or triethanolamonium, particularly sodium dodecyl-benzenesulphonate; fatty alcohol sulfates with a linear or branched aliphatic chain bearing 8 to 18 carbon atoms, the cation being selected from the group of sodium, ammonium, mono-, di- and triethylammonium, particularly sodium laurylsulfate; ethersulfates including polyethoxylated derivatives of the above alcohol sulfates, the number of ethoxy rests being between 1 and 4; and mixtures thereof.

metal salts including aluminum, calcium, potassium, and iron salts; and pharmaceutically acceptable combinations of the above, particularly mixtures of egg albumin and microcrystalline cellulose or mixtures of non-ionic and anionic surfactants, particularly sodium lauryl sulphate and sorbitol monooleate or sodium lauryl sulphate and coconut fatty acid diethanolamide.

It must be noted, of course, that only approved foam stabilizers may be used for the production of foam soft gelatin capsules for food or pharmaceutical uses. The utilization of following optional materials, mixed with the gelatin melt before generation of the gelatin foam, provides soft gelatin capsules with optimal or specific qualities without destroying or substantially altering their valuable physical properties:

preservatives, including sulfur dioxide, methylparaben, propylparaben, sodium propionate and mixtures thereof, generally at a concentration of between about 0.01 to 2%, based upon the weight of dry gelatin;

food or pharmaceutically acceptable coloring agents selected from synthetic dyes, particularly azo-dyes, and certified lakes, iron oxides and hydroxides, titanium dioxide, and natural dyes used alone or in combination in varying amounts; in concentrations of between about 0.001 to 10%, based upon the weight of dry gelatin;

flavoring agents, for example ethyl vanillin and essential oils, to impart desirable odors to capsules or for taste purposes in chewable capsules, and flavoring agents accepted for food and pharmaceutical use, usually prepared by or derived from synthetic flavor oils and/or oils derived from plants, leaves, flowers, fruits, etc. as well as combinations thereof. Representative flavor oils include peppermint oil, cinnamon oil, spearmint oil, etc. Furthermore, natural or synthetic fruit flavors, particularly oils including lime, grape, orange, lemon, grapefruit and fruit essence including apple, pineapple, cherry, strawberry, etc. can be used. The above flavoring agents are preferably used at a concentration of about 0.01 to about 6% by weight of the dry gelatin;

sugar and related sweetening substances, to impart chewable characteristics to the capsule shell, at a concentration of between about 0.1 to 15% by weight of the dry gelatin; and medicaments, in specific cases where certain highly active, relatively inexpensive compounds, such as benzocaine in chewable cough capsules (about 3mg per capsule shell), are formulated in single doses.

In addition, it has been found that the foam soft gelatin capsules of the present invention can be produced with various grades of gelatin combined with extenders of between about 2 to 40% content, by weight selected from the group of sunflower proteins, soybean proteins, cotton seed proteins, peanut proteins, rape seed proteins, and better defatted qualities thereof; as well as native starches, especially potato and corn starches, or derivatives thereof, including pregelatinized starches, thin-boiling starches, dextrins, and hydroxyalkylstarches. For manufacturing foam soft gelatin capsules with such gelatin extenders, and combinations thereof, the same kind of foam stabilizers and optional additives as listed above, are also suitable.

The foam soft gelatin capsules obtained in accordance with the present invention have a wall structure characterized by a homogeneous microdispersion of gas bubbles in plasticized gelatin. The amount of gas in the wall of dry foam soft gelatin capsules may be up to 75% by volume, but is best in a range of 30 to 65% by volume. This doesn't restrain the range of potential uses of the new soft gelatin capsules when compared to conventional soft gelatin capsules. The wall elasticity is similar to, and the closed cell structure of the bubbles of the wall makes the foam soft gelatin capsules as tight as, conventional soft gelatin capsules; making them suitable for the dosage of oxygen sensitive substances, like vitamins. The foam soft gelatin capsules are adapted for the dosage of all kinds of substances encapsulated until now in conventional soft gelatin capsules.

An important advantage of the foam soft gelatin capsules according to the present invention is that they are considerably cheaper to manufacture than conventional soft gelatin capsules because a smaller amount of raw material is required. For example, raw material savings of between 25 to 75% can be reached without substantially altering the mechanical properties of foam soft gelatin capsules. In addition, since the particular structure of the wall of foam soft gelatin capsules provides a considerably increased exchange surface, an appreciable energy saving can be obtained during the manufacturing process because the foam soft gelatin capsule shells dry more easily and more rapidly than the wall of conventional soft gelatin capsules.

As disclosed above, the foam soft gelatin capsules according to the present invention have opaque walls, which effect is due to the homogeneous micronized gas dispersion in the wall material. This avoids the use of opacifying agents such as titanium dioxide or the like.

As described above, it is possible to obtain with foam soft gelatin capsules, within certain limits, controlled shorter disintegration times than with conventional soft gelatin capsules. For example, foam soft gelatin capsules with moderate gas ratios in the wall, as obtained from gelatin foams having gas contents of between approximately 10 to 33% vol/vol, are useful for classical oral administration of medicaments. This means that they can be ingested without particular risk of premature opening in the mouth or in the oesophagus. Their advantage over conventional soft gelatin capsules is a faster disintegration in the stomach, thereby maintaining an improved bioavailability of their contents.

On the other hand, foam soft gelatin capsules with higher gas ratios in the wall are less adapted for classical oral administration since the disintegration is so fast that a premature content release may occur in the mouth or in the oesophagus. This particularly makes them suitable as chewing-capsules, or as capsules for sublingual administration, or in all cases where a fast absorption of the medicament by the mucous membrane of the mouth is desirable, as for nitroglycerin and certain steroid hormones, and particularly for those which are unstable under acidic conditions so as to be destroyed in the stomach.

An effect of the microdispersion of gas bubbles in the wall of foam soft gelatin capsules is to provide a special configuration to the outer surface of the capsule wall (juxtaposed microbubbles) which confers to said capsules, when using current approved natural and synthetic dyestuffs for pharmaceuticals, special and more brilliant color shades, like opalescent or pearly, which cannot be obtained for conventional soft gelatin capsules with the same dyestuffs.

In the pharmaceutical field, for human or veterinary use, foam soft gelatin capsules are not only useful for oral application but are also useful as suppository dosage forms for rectal or vaginal application, or as a specialty package in tube form, for single dose application of topical and ophthalmic preparations; rectal ointments and medication; ear and nose drops.

Foam soft gelatin capsules may also be useful in other fields, such as in the cosmetic industry as a package for perfumes, bath oils, bubble baths, shampoos, breath fresheners, or particularly in those cases where single dosage forms with a fast disintegration would be ideal, such as, for example:

food packaging, as for powdered instant coffee or spices;

candy manufacturing;

fertilization of ornamental plants and/or indoor plants;

packing of sensitive seeds in combination with protective agents and/or fertilizers; and packing of single dyestuff (or mixtures of various dyes) doses, at precise weight for quick preparation of dyestuff solutions.

The present invention is illustrated by the following examples:

EXAMPLE 1

200 liters of gelatin melt was prepared as follows: 39% by weight of a B grade, 150 Bloom strength, gelatin, pharmaceutical grade, was homogeneously mixed with 17.2% by weight of chilled glycerol (USP grade) and 43.8% by weight of chilled deionized water. The aqueous mixture was melted at 80° C. within 4 hours, under reduced pressure. The resulting natural transparent melt was transferred into a tank and kept at 60° C. Its viscosity at this temperature was 3,300 cps.

Gelatin foam was then prepared continuously, as shown in FIG. 1, by injecting controlled flows of the above melt and of air into the mixing head of a continuous pressure beater Air-O-Matic type T, supplied by Air-O-Matic Holland BV, Weesp, Netherlands. The mixing head length was doubled by adjunction of a second identical head. The rotation speed of the rotor was 400 rpm. The injected air and gelatin melt flows were adjusted so as to have at the exit of the continuous pressure beater a homogeneous white opaque gelatin foam flow of about 11.5 kg per hour, characterized by an air content of 33% by volume, a viscosity of 10,200 cps at 60° C. and diameters of the dispersed air bubbles, measured by photomicrography, of between about 10 to 100 microns.

Said gelatin foam was directly fed to the two spreader boxes of a rotary die soft gelatin capsules manufacturing machine, which controlled the flow of said gelatin foam onto two air-cooled rotating drums, where two white opaque gelatin foam ribbons were cast and further processed to white opaque, slightly opalescent, foam soft gelatin capsules, filled with peanut oil (USP grade), at a rate of about 15,000 capsules per hour.

Said foam soft gelatin capsules were first dried in a tumbler dryer with an air blast at 21° C. and 20% relative humidity and then allowed to come to equilibrium with the same forced air conditions on trays in a drying tunnel.

The drying conditions of said foam soft gelatin capsules are compared in TABLE 1 below with those of conventional reference soft gelatin capsules having the same dimensions, wall thickness, peanut oil content, and obtained from a gelatin having the following composition by weight: 46% of gelatin, as above, 20% glycerol and 34% water.

TABLE 1

| Nature of Sample | Water content of capsule wall before drying | Water content of capsule wall after 90 min. drying at 21° C. and 20% RH | Additional time to reach moisture equilibrium with air at 21° C. and 20% RH | Equilibrium moisture content of capsule wall at 21° C. and 20% RH |
|---|---|---|---|---|
| Foam soft gelatin capsules | 43.8% | 14.3% | 3 days | 5.1% |
| Conventional reference soft gelatin capsules | 34% | 20.5% | 5 days | 6.3% |

As shown in TABLE 1, despite an initially higher water content of the capsule wall before drying, the foam soft gelatin capsules are characterized by a substantially higher drying rate than conventional soft gelatin capsules, thereby achieving significant manufacturing cost savings.

The above obtained dried capsules were emptied and traces of peanut oil content removed by 1.1.2-trichloroethane. The mean weight of 10 resulting empty shells of foam soft gelatin capsules is compared in TABLE 2. below, with the mean weight of 10 empty shells of the above described conventional reference soft gelatin capsules.

TABLE 2

| Sample | Weight Evaluation Mean Weight (in grams) | Capsule Shell Thickness ($.10^{-2}$ inches) |
|---|---|---|
| Foam soft gelatin capsules | 0.2173 | 1.20 |
| Conventional reference soft gelatin capsules | 0.3825 | 1.24 |

As shown in TABLE 2, the manufacturing of the foam soft gelatin capsules according to the present invention enables a raw material saving of about 43% when compared with the manufacturing of conventional soft gelatin capsules of the same dimensions and similar capsule shell thickness.

The foam soft gelatin capsules were confirmed to have the desired properties by a standard disintegration test as described in U.S. Pharmacopeia XX and as summarized in TABLE 3, below:

TABLE 3

Compared Disintegration Times in Seconds Between Foam Soft Gelatin Capsules and Conventional Reference Soft Gelatin Capsules

| Sample | Mean Disintegration Time (on 6 capsules) | Capsule Shell Thickness ($.10^{-2}$ inches) |
|---|---|---|
| Foam soft gelatin capsule | 220 sec. | 1.20 |
| Conventional reference soft gelatin capsule | 320 sec. | 1.24 |

As TABLE 3 shows, the disintegration time of foam soft gelatin capsules is about 31% shorter than for conventional soft gelatin capsules of the same dimension, similar capsule shell thickness and same liquid content.

EXAMPLE 2

Foam soft gelatin capsules were produced as in Example 1, except that the initial gelatin melt had the following composition by weight: 37% gelatin, 16.3% glycerol 46.7% water, and the gelatin foam contained 50% by volume of microdispersed air. The disintegration time of said foam soft gelatin capsules is compared in TABLE 4, below, to the values found for the capsules of Example 1:

TABLE 4

Disintegration Time as a Function of Air Content (on every 6 capsules)

| Sample | Air Content by Volume of the Gelatin Foam Before Drying | Mean Disintegration Time (in sec.) | Capsule Shell Thickness ($.10^{-2}$ inches) |
|---|---|---|---|
| Foam soft gelatin capsules (Example 2) | 50% | 163 sec. | 1.21 |
| Foam soft gelatin capsules (Example 1) | 33% | 220 sec. | 1.20 |
| Conventional reference soft gelatin | 0% | 320 sec. | 1.24 |

TABLE 4-continued

| | Disintegration Time as a Function of Air Content (on every 6 capsules) | | |
|---|---|---|---|
| Sample | Air Content by Volume of the Gelatin Foam Before Drying | Mean Disintegration Time (in sec.) | Capsule Shell Thickness ($.10^{-2}$ inches) |
| capsules | | | |

TABLE 4 above demonstrates that, with a suitable choice of the air proportion in the capsule wall, it is possible within certain limits to control the disintegration time of foam soft gelatin capsules.

EXAMPLE 3

The production of colored foam soft gelatin capsules was as in Example 1, but before foam generation, the following dyes were mixed with the natural transparent gelatin melt at a concentration of 0.5% based upon weight of the dry gelatin.
Red: Azorubin (C.I. Food Red 3)
Blue: Patent Blue (C.I. Food Blue III)

The colored foam soft gelatin capsules were opaque and had similar disintegration times as the corresponding white opaque foam soft gelatin capsules described in Example 1 above.

In addition, the colored foam soft gelatin capsules were characterized by new, more brilliant, opalescent-like color shades than for conventional soft gelatin capsules.

EXAMPLE 4

Example 2 was repeated by adding the following components in the gelatin melt before foam generation: (percentages given are by weight of dry gelatin)
0.8% of peppermint oil as a flavoring agent;
0.2% of sodium lauryl sulphate and 0.2% of sorbitan monooleate as gelatin foam stabilizers;
0.5% of a mixture of methylparaben (4 parts) and propylparaben (1 part) as preservatives.

The additives did not affect the ability to generate a suitable gelatin foam, and the disintegration time of the resulting flavored capsules remained similar to Example 2.

While there have been described and illustrated several embodiments of the present invention, the scope and working range of the invention shall not be limited by the examples given above. The invention comprises as well various changes and modifications which will occur to those skilled in the art.

It is intended in the appended claims to cover all such changes and modifications as fall within the true spirit and scope of the present invention.

What is claimed is:

1. A method for the production of foam soft gelatin capsules, which method comprises the steps of:
    A. mixing dry gelatin and one or more plasticizers with water to make an aqueous mixture;
    B. melting the aqueous mixture at a temperature range of between 65° to 95° C. to make a gelatin melt;
    C. mixing a gas into the gelatin melt to make a gaseous gelatin melt;
    D. microdispersing the gas into the gaseous gelatin melt to make a gelatin foam to provide a bubble diameter of 0.1 to 200 microns; and
    E. molding the gelatin foam into foam soft gelatin capsules having a bubble diameter of 0.1 to 200 microns.

2. The method of claim 1 wherein in step A the gelatin is in a pH range of between about 4.0 to 10.0.

3. The method of claim 1 wherein in step A the gelatin is in a pH range of between about 4.0 to 7.0.

4. The method of claim 1 wherein in step A the ratio by weight of water to gelatin in the aqueous mixture is in a range of between about 0.8 to 1.6.

5. The method of claim 1 wherein in step A the ratio by weight of water to gelatin in the aqueous mixture is in a range of between about 1 to 1.3.

6. The method of claim 1 wherein in step A the plasticizer is selected from a group consisting of:
    poly-hydroxy-alcohols consisting of glycerol, sorbitol, and mannitol;
    dialkylphthalates preferably where alkyl is butyl;
    lower alkyl citrates wherein lower alkyl has 1 to 6 carbon atoms;
    glycols and polyglycols consisting of polyethyleneglycol with a molecular weight range of about 200 to 40,000 dalton, methoxy-propylene-glycol, and 1,2-propyleneglycol;
    esters of polyhydroxy-alcohols consisting of mono-, di- and tri-acetate of glycerol;
    ricinoleic acid and esters thereof; and
    mixtures of the above.

7. The method of claim 1 wherein in step A the ratio by weight of dry plasticizer to dry gelatin in the aqueous mixture is in a range of between about 0.3 to 1.8.

8. The method of claim 1 wherein in step A, the ratio by weight of dry plasticizer to dry gelatin in the aqueous mixture is in a range of between about 0.4 to 0.75.

9. The method of claim 1 wherein in step C the gas is a gas selected from a group consisting of carbon dioxide, oxygen, air, nitrogen, argon or a mixture thereof.

10. The method of claim 1 wherein in step C the gas is air.

11. The method of claim 1 wherein in step D the microdispersion of the gas into the gaseous gelatin melt is accomplished mechanically by beating or whipping equipment.

12. The method of claim 1 wherein in step D the microdispersion of the gas into the gaseous gelatin melt is accomplished by simultaneous treatment of controlled quantities of the gas and the gaseous melt respectively in a continuous pressure beater.

13. The method of claim 1 wherein in step D the microdispersion of the gas into the gaseous gelatin melt is accomplished by a centrifugal emulsifier combined with a controller to regulate addition of gas and of water into the gelatin foam.

14. The method of claim 1 wherein in step D the microdispersion of the gas into the gaseous gelatin melt is accomplished within a container fitted with a heat exchanger-cooling system to avoid premature gelling of foam or degradation thereof.

15. The method of claim 1 wherein in step D the gelatin foam is characterized by a gas content range between about 10 to 66% by volume, a viscosity range between about 1,000 to 30,000 centipoises when measured at 60° C., and by air bubbles having a diameter range between about 0.1 to 200 microns.

16. The method of claim 1 wherein in step D the gelatin foam is characterized by a gas content range between about 23 to 56% by volume, a viscosity range between about 5,000 to 15,000 centipoises when measured at 60° C., and by air bubbles having a diameter range between about 1 to 50 microns.

17. The method of claim 1 wherein in step D the gelatin foam is maintained at a temperature range between about 40° to 95° C.

18. The method of claim 1 wherein in step D the gelatin foam is maintained at a temperature range between about 55° to 70° C.

19. The method of claim 1 wherein in any of the steps A, B, C or D a foam stabilizing agent is added having a concentration range of between about 0.01 to 5.0% based upon the weight of the dry gelatin.

20. The method of claim 1 wherein in any of the steps A, B, C or D a preservative is added having a concentration range of between about 0.01 to 2% based upon the weight of dry gelatin.

21. The method of claim 1 wherein in any of the steps A, B, C or D a coloring agent is added having a concentration range of between about 0.001 to 10% based upon the range of the gelatin.

22. The method of claim 1 wherein in any of the steps A, B, C or D a flavoring agent is added having a concentration range of between about 0.01 to 6% based upon the weight of the dry gelatin.

23. The method of claim 1 wherein in any of the steps A, B, C or D a sweetening substance is added having a concentration range of between about 0.1 to 15% based upon the weight of the dry gelatin.

24. The method of claim 1 wherein in any of the steps A, B, C or D a medicament is added.

25. The method of claim 1 wherein in step A a gelatin extender is added having a concentration range of between about 2 to 40% based upon the total weight of dry gelatin and dry gelatin extender.

26. The method of claim 25 wherein the gelatin extender is selected from a group of proteins consisting of sunflower proteins, soybean proteins, cotton seed proteins, peanut proteins and rape seed proteins.

27. The method of claim 26 wherein the proteins are defatted.

28. The method of claim 25 wherein the gelatin extender is selected from starches consisting of native starches and derivatives thereof, including pre-gelatinized starches, thin-boiling starches, dextrins and hydroxyalkyl starches.

29. Foam soft gelatin capsules comprising gelatin and one or more plasticizers and having a gas microdispersed therein with bubbles of 0.1 to 200 microns.

30. Foam soft gelatin capsules of claim 29 for the dosage of liquid, pasty or solid contents.

31. Foam soft gelatin capsules of claim 29 for the dosage of pharmaceutical, fertilizer, seed, candy, cosmetic, food or dyestuff contents.

32. Foam soft gelatin capsules of claim 29 for oral, rectal, vaginal, topical or ophthalmic applications.

33. Foam soft gelatin capsules of claim 29 for chewable applications.

* * * * *